(12) United States Patent
Stucky et al.

(10) Patent No.: US 8,202,549 B2
(45) Date of Patent: Jun. 19, 2012

(54) MESOCELLULAR OXIDE FOAMS AS HEMOSTATIC COMPOSITIONS AND METHODS OF USE

(75) Inventors: Galen Stucky, Santa Barbara, CA (US); Sarah Baker, Santa Barbara, CA (US); April Sawvel, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 679 days.

(21) Appl. No.: 12/191,257

(22) Filed: Aug. 13, 2008

(65) Prior Publication Data

US 2009/0047329 A1 Feb. 19, 2009

Related U.S. Application Data

(60) Provisional application No. 60/955,854, filed on Aug. 14, 2007.

(51) Int. Cl.
*A61K 9/70* (2006.01)

(52) U.S. Cl. ......... 424/684; 427/443; 427/446; 427/447

(58) Field of Classification Search .................. 424/401
See application file for complete search history.

(56) References Cited

U.S. PATENT DOCUMENTS

| | | | |
|---|---|---|---|
| 4,373,519 A | 2/1983 | Errede et al. | |
| 4,748,978 A | 6/1988 | Kamp | |
| 4,822,349 A | 4/1989 | Hursey et al. | |
| 5,922,299 A * | 7/1999 | Bruinsma et al. | 423/335 |
| 6,162,241 A | 12/2000 | Coury et al. | |
| 2003/0133990 A1 | 7/2003 | Hursey et al. | |
| 2005/0058721 A1 | 3/2005 | HUrsey | |
| 2005/0074505 A1 | 4/2005 | Hursey | |
| 2006/0078628 A1 | 4/2006 | Koman et al. | |
| 2006/0141060 A1 | 6/2006 | Hursey et al. | |
| 2006/0155235 A1 | 7/2006 | Sawyer et al. | |
| 2006/0211965 A1 | 9/2006 | Horn et al. | |
| 2006/0211971 A1 | 9/2006 | Horn et al. | |
| 2007/0004995 A1 | 1/2007 | Horn et al. | |
| 2007/0031515 A1 | 2/2007 | Stucky et al. | |
| 2007/0104768 A1 | 5/2007 | Huey et al. | |
| 2007/0154564 A1 | 7/2007 | Stucky et al. | |
| 2007/0227351 A1* | 10/2007 | Garcia-Martinez | 95/90 |

FOREIGN PATENT DOCUMENTS

| | | |
|---|---|---|
| WO | 2006088912 | 8/2006 |
| WO | 2006110393 | 10/2006 |
| WO | WO 2006/135339 | * 12/2006 |
| WO | 2007022264 | 2/2007 |

OTHER PUBLICATIONS

Carrado, et al. (2004) "Effects of Surface Functionalization and Organo-Tailoring of Synthetic Layer Silicates on the Immobilization of Cytochrome c" Chemistry of Materials 16:2559-2566.
Ha, et al. (2000) "Facile Assembly of Zeolite Monolayers on Glass, Silica, Alumina, and Other Zeolites Using 3-Halopropylsilyl Reagents as Covalent Linkers" Adv. Mater. 12(15):1114-1117.
Han, et al. (2007) "Spherical Siliceous Mesocellular Foam Part cles for High-Speed Size Exclusion Chromatography" Chem. Mater. 19(9):2292-2298.
Jerez, et al. (2006) "Coating of Silica Sand with Aluminosilicate Clay" J. Colloid Interface Sci. 294(1):155-164.
Lin, et al. (2007) "Spherical Siliceous Mesocellular Foam Particles for High-Speed Size Exclusion Chromatography" Langmuir 23(4):1995-1999.
Liu, et al. (2003) "Synthesis and Characterization of Kaolin/NaY/MCM-41 Composites" Microporous and Mesoporous Materials 66:117-125.
Schmidt-Winkel, et al. (1999) "Mesocellular Siliceous Foams with Uniformity Sized Cells and Windows" J. Amer. Chem. Soc. 121(1):254-255.
Schmidt-Winkel, et al. (2000) "Microemulsion Templates for Mesoporous Silica" Langmuir. 16(2):356-361.
Yoon (2007) "Organization of Zeolite Microcrystals for Production of Functional Materials" Acc. Chem. Res. 40 (1):29-40.

* cited by examiner

*Primary Examiner* — Gina C Yu
(74) *Attorney, Agent, or Firm* — Rudy J. Ng; Carol L. Francis; Bozicevic, Field & Francis LLP

(57) ABSTRACT

The present invention relates to hemostatic compositions comprising a mesocellular oxide foam and, optionally, a biologically active agent such as a procoagulant, as well as devices and methods of use to promote blood clotting.

16 Claims, 10 Drawing Sheets

50 nm

US 8,202,549 B2

MESOCELLULAR OXIDE FOAMS AS HEMOSTATIC COMPOSITIONS AND METHODS OF USE

CROSS REFERENCE TO RELATED APPLICATIONS

This application claims the benefit of provisional application No. 60/955,854, filed Aug. 14, 2007, the entire contents of which is incorporated herein by reference.

STATEMENT REGARDING FEDERALLY SPONSORED RESEARCH

The U.S. government may have certain rights in this invention, pursuant to grant nos. ONR # N00014-06-1-0145, awarded by the Office of Naval Research.

BACKGROUND

Treatment of bleeding wounds, particularly severely bleeding wounds, can require immediate attention to bring the bleeding under control. Severe bleeding poses a very real risk of death to the casualty if not treated quickly. Although loss of about 10-15% of total blood volume can be endured without clinical sequalae in a healthy person, if a laceration or penetrating trauma (e.g., knife or gun wound) is severe enough or involves critical arteries or veins, this volume of blood can be lost in a matter of minutes. The bleeding must be slowed immediately or irreversible damage to organs and mortality can result.

Bleeding wounds, even those that may be less severe, can pose serious difficulties and risks when a severe wound is inflicted in a remote area or other situations (such as found in a battlefield) where full medical assistance may be not immediately available. In such circumstances it can be critical to undertake measures to slow or stop bleeding so that the subject can be transported to a medical facility.

Various methods and hemostatic compositions for promoting blood clotting have been developed, and can be applied to help control bleeding in such situations. Exemplary compositions include those composed of bound zeolite (see, e.g., U.S. Pat. No. 4,822,349). Such zeolite/binder compositions, such as QuikClot®, can have a water content of about 1.54% or less as estimated by measuring the mass of material before and after heating at 550° C. (i.e., Loss on Ignition (LOI) at 550° C.). Higher temperatures are sometimes used for LOI calculations, but procedures that utilize these higher temperatures increase the loss of chemical compounds other than water. Further exemplary hemostatic compositions include those that composed of partially hydrated zeolite, such as described in US 2005/0059721.

The field continues to develop additional hemostatic compositions that provide for, for example, rapid initiation of blood clotting, increased rate of blood clotting, sufficient blood clot strength, and/or reduced adverse side effects (e.g., due to heat that can be generated locally as a result of enthalpy of hydration that may be associated with use of certain hemostatic agents, such as dry bound zeolite), and which can optionally deliver antibiotics and/or wound healing-promoting agents, and/or pro-thrombotic agents, and/or ions. Of particular interest are such hemostatic compositions that can be rapidly and safely applied in an emergency situation, such as on the battlefield or at the scene of an accident, without the need for intensive training or equipment.

LITERATURE

U.S. Pat. Nos. 4,748,978; 4,822,349; 4,373,519; US 2003/0133990; US 2005/0074505; US 2005/0058721; US 2006/0141060; US 2007/0004995; US 2006/0211971; US 2006/0211965; US 2006/007862; US 2006/0155235; WO 06/088912; US 2007/0031515; US 2007/0154564; WO 06/110393; WO 07/022,264.

Jerez et al. "Coating of silica sand with aluminosilicate clay." Journal of Colloid and Interface Science 2006, 294(1): 155-164; Liu et al. Microporous and Mesoporous Materials 2003, 66:117; Ha et al. Advanced Materials 2000, 12, 1114; and Yoon Accounts of Chemical Research 2007, 40:29; Lin et al. (2007) "Preparation of Protein-Silicate Hybrids from Polyamine Intercalation of Layered Montmorillonite." Langmuir 23:1995-1999; Carrado et al. (2004) "Effects of Surface Functionalization and Organo-Tailoring of Synthetic Layer Silicates on the Immobilization of Cytochrome c." Chemistry of Materials 16:2559-2566; Schmidt-Winkel et al. J. Amer. Chem. Soc. 1999, 121, 254; Schmidt-Winkel et al. Langmuir. 2000, 16, 356-36.

SUMMARY

The present invention relates to hemostatic compositions comprising a mesocellular oxide foam and, optionally, a biologically active agent such as a procoagulant, as well as devices and methods of use to promote blood clotting.

The disclosure provides, for example, a hemostatic composition comprising a hemostatically effective amount of a sterile, mesocellular oxide foam, wherein the mesocellular foam is characterized by an average pore size of from about 10 nm to 100 nm. In related embodiments, the mesocellular foam is characterized by an average pore size of from about 15 nm to 90 nm, from about 15 nm to 80 nm, from about 15 nm to 40 nm, from about 15 nm to 35 nm, or from about 20 nm to 35 nm. In further related embodiments, the mesocellular foam comprises a bound biologically active agent, which may be covalently or non-covalently bound to the mesocellular foam. In specific exemplary embodiments, the biologically active agent is a clot promoting agent, such as thrombin.

The disclosure further provides a thrombin-loaded mesocellular oxide foam comprising at least 5% by weight thrombin. In related embodiments, the mesocellular foam is characterized by an average pore size of from about 1 nm to 100 nm, with mesocellular foam having an average pore size of from about 10 nm to 100 nm being of interest. In related embodiments, the thrombin-loaded mesocellular foam comprises at least 10% or at least 25% by weight thrombin.

The disclosure also provides a medical device comprising a hemostatic composition described herein (e.g., a mesocellular oxide foam which may optionally be loaded with a biologically active agent, such as thrombin), and a sterile substrate on which the hemostatic composition is disposed. In related embodiments, the substrate is adapted for delivery of the hemostatic composition to a bleeding wound. Exemplary substrates include a bandage or sponge.

The disclosure further provides methods of clotting blood flowing from a wound comprising applying to a wound in a subject a hemostatic composition described herein (e.g., a mesocellular oxide foam which may optionally be loaded with a biologically active agent, such as thrombin) and maintaining the hemostatic composition in contact with the wound for a period of time sufficient to at least initiate blood clotting.

The disclosure also provides methods of making a hemostatic composition, the method comprising contacting a mesocellular oxide foam (e.g., characterized by an average pore size of from about 10 nm to 100 nm) with a solution containing a biologically active agent, said contacting being for a time sufficient to provide for adsorption or absorption of the biologically active agent to the mesocellular foam;

wherein a hemostatic composition comprising the mesocellular oxide foam and bound biologically active agent is produced. In related embodiments, the biologically active agent-loaded mesocellular oxide foam is washed with a buffer to remove un-bound biologically active agents. In further exemplary embodiments the method comprises packaging the hemostatic composition in a container adapted to retain sufficient moisture to facilitate maintenance of activity of the biologically active agent.

These and other embodiments of the invention will be readily apparent to the ordinarily skilled artisan upon reading the present specification.

BRIEF DESCRIPTION OF THE DRAWINGS

FIG. 10(b) inset is a graph of time-dependent absorbance due to cleavage of chromogenic substrate for thrombin.

FIG. 11 inset is a rescaled view of data immediately beneath the inset.

DEFINITIONS

Figure 1:
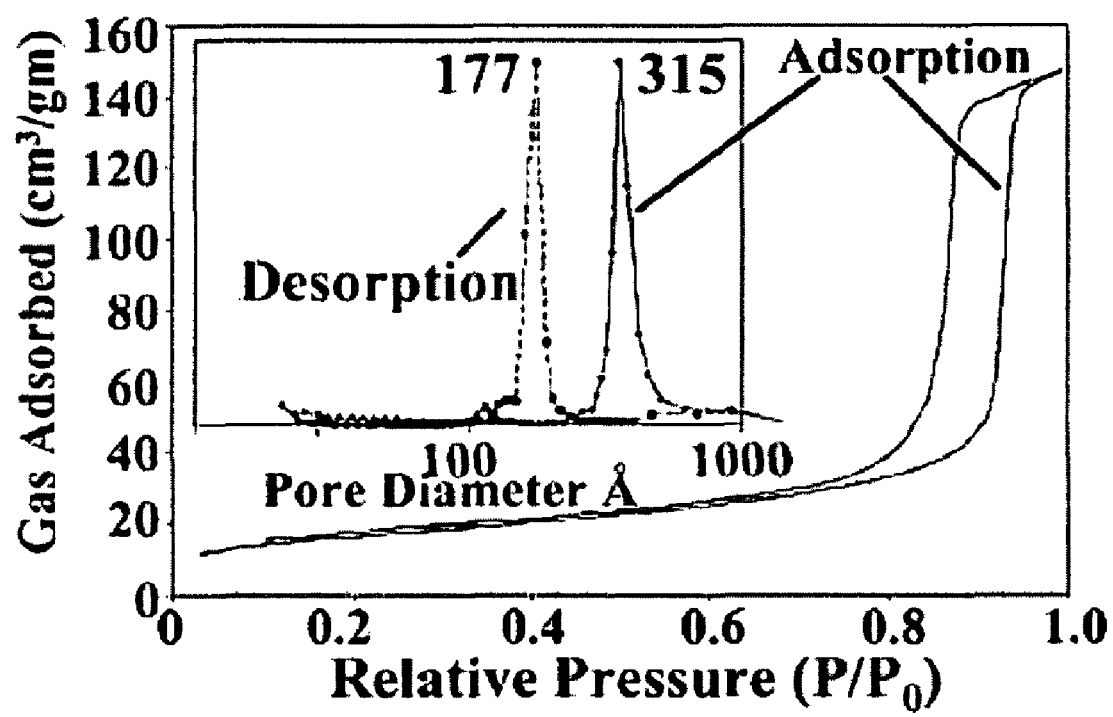
FIG. 1 is a graph showing N2 adsorption/desorption isotherms and calculated pore dimensions for Mesocellular Foam.

"Mesocellular foam", "mesoporous cellular foam", "mesocellular oxide foam", and "mesoporous oxide foam" are used interchangeably to refer to a high-surface area, porous oxide material composed of an oxide of silicon, aluminum, transition metal (e.g. titanium, zirconium, and the like), aluminosilicate, or combination thereof, wherein the mesocellular foam has an average pore size of not greater than about 100 nm as calculated using the BET calculation based on the N2 adsorption/desorption isotherm.

A "hemostatic agent" refers to an agent which promotes blood clotting, e.g., following administration to a wound. Hemostatic agents encompass, for example, inorganic materials (e.g., silicon oxides having the physical characteristics of a mesocellular foam as described herein), as well as biologically active ions (e.g., ions that act as cofactors in the clotting cascade (e.g., by serving as an ionic bridge), and/or facilitated colloid precipitation (e.g., red blood cell precipitation), clotting factor proteins (e.g., thrombin, etc.), and the like.

A "hemostatic composition" refers to a composition comprising at least one hemostatic agent, and further includes at least one or more additional components, which may be hemostatically active (e.g., promote blood clotting or promote activity of the hemostatic agent in the hemostatic composition in blood clotting). Hemostatic compositions can also contain agents that are hemostatically inert.

The term "hemostasis" as used herein refers to inhibition of bleeding, including the arrest of bleeding, which is accompanied by blood clot formation.

A "hemostatically effective amount" refers to an amount of a hemostatic composition which, following application to a bleeding wound, is effective to facilitate blood clotting (e.g., as compared to time to clot formation in the absence of the hemostatic agent), increase blood clotting rate as compared to a blood clotting rate in the absences of the hemostatic agent, and/or improve blood clot strength as compared to blood clot strength in the absence of the hemostatic agent. Clot strength can be measured by Thrombelastograph® measurements. Assays for assessing hemostatic activity are known in the art, with exemplary methods described herein.

The term "isolated" means the compound is present in an environment other than that in which it is found in nature. "Isolated" is meant to include compounds that are within samples that are substantially enriched for the compound of interest and/or in which the compound of interest is partially or substantially purified.

As used herein, the term "purified" refers to a compound that is removed from its natural environment and is at least 60% free, preferably 75% free, and most preferably 90% free from other components with which it is naturally associated.

The terms "individual," "subject," "host," and "patient," used interchangeably herein, refer to any subject in need to treatment, e.g., mammals, including, but not limited to, humans, simians, felines, canines, equines, bovines, mammalian farm animals, mammalian sport animals, and mammalian pets. Human subjects in need of treatment are of particular interest.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a hemostatic agent" includes a plurality of such agents and reference to "the hemostatic agent" includes reference to one or more agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS OF THE INVENTION

Embodiments of the present invention relate to hemostatic compositions which comprise a mesocellular oxide foam and, optionally, a second hemostatic agent such as thrombin, as well as methods as well as devices and methods of use to promote blood clotting.

Mesocellular Foams

Mesocellular foams for use as hemostatic agents in the hemostatic compositions and methods disclosed herein are high-surface area compositions composed of an oxide of silicon, aluminum, transition metal (e.g., titanium, zirconium, and the like), aluminosilicate, or combination thereof, and are generally characterized by a porous internal architecture, which architecture can be tailored to provide for desired structural features, e.g., pore size (e.g., pore diameter), pore size distribution, pore geometry, pore ordering, inter-connectedness of pores, and surface area (i.e., both internal surface area, as determined by the BET calculation based on $N_2$ desorption/adsorption isotherms, and biologically accessible surface area, which is that internal surface area accessible to blood constituents). Mesocellular foams of silicon oxide are of particular interest.

Mesocellular foam can be produced and/or selected according to desired physical parameters of pore size, pore geometry, pore ordering (e.g. disordered, hexagonal, cubic, lamellar, worm-like, and the like), surface charge (as determined by electrophoretic zeta potential measurements), surface area (e.g., both internal surface area, as determined by the BET calculation based on $N_2$ desorption/adsorption isotherms, and biologically accessible surface area, which includes that internal surface area accessible to blood constituents), inter-connectedness of pores (2-dimensional, 3-dimensional, and the like), crystallinity, hydration capacity, modifications (e.g. combination with a clot promoting agent, ion-exchanged (e.g., with calcium or other ions as exemplified herein), addition of salts, hydration state, and the like as exemplified further herein) and the like which can influence parameters of blood clotting activity upon application of the hemostatic agent to a subject.

The isoelectric point of a metal oxide determines the surface charged expressed by the metal oxide in a given media. For example, silicon dioxide is characterized by an isoelectric point that can range between 1 to 3. When immersed in blood, which is buffered to a pH between 7.3-7.4, silicon dioxide will initially present a negatively charged surface since the isoelectric point of silicon dioxide is less than the pH of blood (e.g., less than about 7.3 pH). Those oxides with an isoelectric point below the pH of blood are disclosed to be pro-coagulants in US 2007/0154564, which is incorporated herein by reference.

As used herein, "isoelectric point" refers to the pH at which the zeta-potential equals zero in an aqueous electrolyte such as 2 mM $CaCl_2$. The zeta potential is the surface charge density of a metal oxide in aqueous suspension, measured as a function of pH by the electrophoretic method using the Smoluchowski equation (Cocera, M. et al., Langmuir 1999, 15, 2230-2233). Unless specifically indicated otherwise, the zeta potential of the metal oxide is measured in a $CaCl_2$ electrolyte that mimics the $Ca^{2+}$ concentration in blood.

The pore size of the mesocellular foam can be selected to provide for desired clot-promoting activity (e.g., clotting rate, clotting time, clot strength, etc.). Average pore size is generally determined by the BET-BJH calculation of $N_2$ desorption/adsorption isotherm data. In one embodiment, the average pore size of the mesocellular foam is from about 10 to 100 nm, about 15 nm to 100 nm, about 15 nm to 90 nm, about 15 nm to 80 nm, about 15 nm to 40 nm, about 15 nm to 35 nm, about 20 nm to 35 nm. In further exemplary embodiments, the mesocellular foam has an average pore size of greater than 10 nm, greater than 15 nm, greater than 20 nm, greater than 25 nm, or greater than 30 nm, with the proviso that the average pore size is less than about 100 nm. In other examples, the mesocellular foam has an average pore size of about 10-50 nm, about 20-50 nm, about 20-40 nm, about 20-35 nm, about 33-40 nm, about 25-50 nm, and the like. In exemplary embodiments, the mesocellular foam has an average pore size of about 10 nm, about 15 nm, about 20 nm, about 25 nm, about 30 nm, or about 35 nm.

The pore opening diameter (i.e., pore window size) may facilitate the access of clotting enzymes to the internal surface area and also provide access for the adsorption of clot-promoting enzymes or therapeutic agents within the material pores that may facilitate clotting. A wide range of pore window sizes can be selectively created to promote access of thrombin and other enzymes into the MCF pore structure. In certain embodiments, the mesocellular foam has an average pore window size of at least 11 nm, such as at least 20 nm, including at least 25 nm. In some cases, the mesocellular foam has an average pore window size ranging from about 11 nm to about 35 nm, such as from about 20 nm to about 35 nm, including from about 25 nm to about 35 nm.

In certain cases, the mesocellular foam has an average pore volume of at least 1 $cm^3/g$, such as at least 1.4 $cm^3/g$, including at least 2 $cm^3/g$. In some cases, the mesocellular foam has an average pore volume ranging from about 1 $cm^3/g$ to about 2.5 $cm^3/g$, such as from about 1.4 $cm^3/g$ to about 2.5 $cm^3/g$, including from about 2 $cm^3/g$ to about 2.5 $cm^3/g$.

In exemplary embodiments, the mesocellular foam has an average pore window size of at least 11 nm, and an average pore volume of at least 1 $cm^3/g$, such as at least 1.4 $cm^3/g$, including at least 2.5 $cm^3/g$. In further exemplary embodiments, the mesocellular foam has an average pore window size of at least 11 nm, and an average pore volume of ranging from about 1 $cm^3/g$ to about 2.5 $cm^3/g$, such as from about 1.4 $cm^3/g$ to about 2.5 $cm^3/g$, including from about 2 $cm^3/g$ to about 2.5 $cm^3/g$. In other embodiments, the mesocellular foam has an average pore window size ranging from about 11 nm to about 35 nm, and an average pore volume of at least 1 $cm^3/g$, such as at least 1.4 $cm^3/g$, including at least 2.5 $cm^3/g$. In some cases, the mesocellular foam has an average pore window size ranging from about 11 nm to about 35 nm, and an average pore volume of ranging from about 1 $cm^3/g$ to about 2.5 $cm^3/g$, such as from about 1.4 $cm^3/g$ to about 2.5 $cm^3/g$, including from about 2 $cm^3/g$ to about 2.5 $cm^3/g$. In other examples, the mesocellular foam has an average pore volume of at least 1 $cm^3/g$, and an average pore window size of at least 11 nm, such as at least 20 nm, including at least 35 nm. In some cases, the mesocellular foam has an average pore volume of at least 1 $cm^3/g$, and an average pore window size ranging from about 11 nm to about 35 nm, such as from about 20 nm to about 35 nm, including from about 25 nm to about 35 nm. In certain embodiments, the mesocellular foam has an average pore volume ranging from about 1 $cm^3/g$ to about 2.5 $cm^3/g$, and an average pore window size of at least 11 nm, such as at least 20 nm, including at least 35 nm. In some examples, the mesocellular foam has an average pore volume ranging from about 1 $cm^3/g$ to about 2.5 $cm^3/g$, and an average pore window size ranging from about 11 nm to about 35 nm, such as from about 20 nm to about 35 nm, including from about 25 nm to about 35 nm.

As noted above, mesocellular foams that find use in the compositions and methods disclosed herein include an oxide of silicon; aluminum; transition metal (e.g., titanium, zirconium, and the like); aluminosilicate; or combination thereof. Exemplary materials for production of mesocellular foams include, but are not necessarily limited to, silicon dioxide, titanium dioxide, silicon-aluminum-oxide, aluminum oxide, and the like.

Methods of Making Mesocellular Foam

Methods for making mesocellular foam are available in the art, and can be readily applied to the production of mesocellular foam for use in the hemostatic composition of the present disclosure. For example, mesocellular foams can be prepared by sol-gel condensation of oxide precursors around structure directing agents. Additionally, mesocellular foams can be prepared by a hydrothermal, or autoclave, process. (see, e.g., Han et al. (2007) Chem. Mater. 19:2292-2298). In these methods, one or more structure-directing agents and oxide precursors are mixed such that the oxide precursors "crystallize" around the structure-directing agent.

Oxide precursors for use in the sol-gel mesocellular foam production method can be selected according to a desired final mesocellular foam composition. Exemplary oxide precursors include metal alkoxides (e.g., silicon dioxide can be prepared from the silicon alkoxide precursor, tetraethylorthosilicate (TEOS); titanium dioxide can be prepared from the titanium alkoxide precursor, titanium isopropoxide or titanium tetra-ethoxide; aluminum oxide can be prepared from the aluminum alkoxide, aluminum isopropoxide) and metal halides (e.g., silicon dioxide can be prepared from the silicon halide precursor, silicon chloride ($SiCl_4$; titanium dioxide can be prepared from the titanium halide precursor, titanium chloride ($TiCl_4$)). Where the mesocellular foam is to include a combination of oxides, the ratios of the oxide precursors can be varied to provide a desired ratio of oxides in the final mesocellular foam.

Structure directing agents for use in sol-gel mesocellular foam production can be selected from a variety of polymers, block co-polymers, self-assembling polymers, nanoparticles, biologically active agents, and the like, according to the desired geometry of the final mesocellular foam produced. In one embodiment, the structure directing agents are self-assembling block co-polymers such as the Pluronics P123® or F127®.

In general, the surface area, pore size, pore size distribution, pore geometry, and inter-connectedness of pores can be tailored by varying the ratio of inorganic precursor to structure directing agent as well as by incorporating various organic molecules to influence organization of the structure-directing agent (e.g., to affect the association of molecules of the structure-directing material, structure-directing agent folding, and the like). For example, a polymer-swelling agent (e.g., 1,3,5 trimethyl benzene) finds use in affecting the organization of block co-polymers, and can be used in varying amounts relative to the block co-polymer to influence the internal structure of the resulting mesocellular foam.

An exemplary hydrothermal preparation is described by Han et al. (supra). For example, mesocellular foams can be prepared by dissolving a triblock copolymer such as Pluronics P123® (BASF) in an acidic solution (e.g., in 10 mL of 37% hydrochloric acid and 65 mL of water). A polymer-swelling agent, 1,3,5-trimethyl benzene (e.g., 4 g), is added to the mixture and resulting mixture heated (e.g., to 40° C. for 2 hours). The oxide precursor (e.g., 9.2 mL of silicon alkoxide precursor, tetraethylorthosilicate (TEOS)) is added and the resulting mixture was stirred (e.g., for 5 minutes). The resulting mixture is added to a hydrothermal bomb reactor and heated (e.g., to 40° C. for 24 hours). An agent that influences particle shape (e.g., ammonium fluoride (46 mg)) can optionally be added. The resulting mixture is heated (e.g., to 100° C. for 24 hours). The precipitate is then filtered, washed (e.g., with water and ethanol), and dried. The mesocellular foam is then calcined (e.g., at 550° C.) to "burn out" the structure directing polymer and to facilitate or further facilitate crystallization of the oxide.

The pore size of the mesocellular foam can be tailored by varying the amount of organic swelling agent (e.g., 1,3,5-trimethylbenzene), agent that affects particle shape (e.g., ammonium fluoride), and/or synthetic temperature. For example, spherical mesocellular foam can be obtained by not adding ammonium fluoride and instead by adding 1,3,5 trimethyl benzene (e.g., 2.5 g). Additionally, spherical mesocellular foams were produced by aging at 140° C. rather than 100° C.

Additional Agents for Use with Mesocellular Foams in Hemostatic Compositions

The mesocellular foams disclosed herein can be provided alone as a hemostatic composition or can be provided in combination with one or more additional biologically active agents (e.g., hemostatic agents, antibiotics, ions (e.g., calcium, potassium, etc.) and the like). In general, optionally additional agents can include components which may be active or inert with respect to the activity of the hemostatic composition in promoting clotting, or may provide for an additional or different biological activity (e.g., antibacterial, anti-inflammatory, and the like). Such additional agent(s) can be provided in admixture (e.g., in dry or hydrated (e.g., solution) with the mesocellular foam (e.g., in a slurry)) or loaded into the mesocellular foam structure itself.

In some embodiments, the hemostatic composition comprises an additional biologically active agent that can facilitate clotting, wound healing, and/or reduce the risk of infection. Such exemplary additional agents can include a hemostatic agent, an antibiotic, growth factors, cytokines, and the like which can promote wound healing and/or reduce the risk of infection. Such components can be from any suitable source, e.g., a recombinant source of the same or different animal origin as the subject to be treated (e.g., human, bovine, etc.). The mesocellular foam can be loaded with biologically active to provide for biologically active as varying weight percent of the mesocellular foam, e.g., 2%, 5%, 10%, 15%, 20%, 25%, or more.

In some embodiments, the hemostatic composition includes a clot-promoting factor in addition to the mesocellular foam described. For example, the hemostatic compositions can include a clotting factor or platelet activating agent. Exemplary agents include thrombin, Factor VII, Factor VIIa, serotonin, collagen, thromboxane A2, and/or ADP. Such components can be from a recombinant source of the same or different animal origin as the subject to be treated (e.g., human, bovine, etc.).

In some embodiments, the mesocellular foam in the hemostatic composition is modified to include a bound biologically active agent, which may be a protein, an ion, or the like. Hemostatic agents are of particular interest. For example, a mesocellular foam surface (i.e., external and/or internal surface) may be modified to provide for a bound clotting promoting factor (e.g., thrombin, recombinant Factor VIIa), antibiotics (e.g., silver ions), and the like. "Bound" as used in this context (which may be used interchangeably with the term "loaded") is meant to encompass covalent and non-covalent binding, including van der Waals forces, hydrogen bonds, chemisorption, physisorption, electrostatic forces, physical trapping within pores and/or channels of the mesocellular foam, and the like. Thus an agent that is "bound" to a mesocellular foam surface includes binding by absorption, adsorption, adhesion, covalent linkage, and the like.

Biologically active agent-loaded mesocellular foam, such as hemostatic agent-loaded mesocellular foam, can be produced by a variety of different methods. For example, mesocellular foam can be soaked in solution containing one or more agents of interest to provide for absorption of the agent(s) onto a mesocellular foam surface, e.g., within the interstices of the mesocellular foam. Following soaking for a desired period of time (e.g., to provide for a desired amount of agent loaded on and/or into the mesocellular foam), the biologically active agent-loaded mesocellular foam can then be washed to remove unbound material. The loaded mesocellular foam can then be dried or stored in hydrated or partially hydrated form, as may be desired according to the biologically active agent used.

In another example, the mesocellular foam can be heat treated to present a hydroxylated surface for condensation attachment of hydro-group expressing biologically active agents. This production method can provide for covalent binding of biologically active agent (e.g., protein) to an external and/or internal surface of the mesocellular foam.

In another example, the mesocellular foam surface is functionalized with, e.g., organosilanes, amino acids, carboxylic acids, and/or phosphate groups, to promote the non-covalent or covalent binding of an agent of interest. For example, mesocellular foam can be functionalized with amine groups to express a positive surface charge capable of electrostatically attracting negatively charged substituents in solution. Alternatively mesocellular foam can be functionalized with carboxylate groups to express a negative surface charge capable of electrostatically attracting positively charged substituents in solution.

In another example, the oxide surface of mesocellular foam can be functionalized with, e.g., organosilanes, amino acids, amines, carboxylic acids, and/or phosphate groups, to promote the attachment of biologically active materials. For example, silicon dioxide will express a negative surface charged when immersed in a solution with a pH greater than the isoelectric point of silicon dioxide. However, if silicon dioxide is first functionalized by attaching amine groups to the surface of silicon dioxide, the effective surface charge will be positive as a consequence of the positively charged amine groups comprising the periphery. Amine functionalized silica will electrostatically attract negatively charged substituents. Negatively charged silica, absent amine functional groups, would electrostatically repel negatively charged substituents.

Biologically active agents that can find use in the hemostatic composition of the present disclosure, and which may used to provide biologically active agent-loaded mesocellular foam can be selected from a variety of different agents. Exemplary agents include polypeptides (e.g., enzymes (including zymogens and activated enzymes), glycoproteins, peptides, and the like), phospholipids, ions (e.g., ions that act as cofactors in the clotting cascade (e.g., by serving as an ionic bridge), facilitate colloid precipitation (e.g., red blood cell precipitation), and/or have antibiotic activity (e.g., silver), and the like), and other agents that have a biological activity of interest (e.g., clot-promoting agents, antibiotics, anti-inflammatories, and the like). Where the agent is a polypeptide or nucleic acid, the agent may be recombinant or synthetic (i.e., produced by non-genetic methods). Of particular interest are agents that have activity in promoting clotting (e.g., thrombin) and/or antibacterial activity (e.g., silver ions). Biological agents such as polypeptides can be of any suitable origin, e.g., human.

Exemplary biologically active polypeptide agents include, but are not limited to, prothrombin, thrombin, Factor VII, Factor VIIa, Factor XI, Factor XIa, Factor XII, Factor XIIa, Factor XIII, Factor XIIIa, fibrin, collagen, fibrinogen, growth factors (e.g. VEGF, epidermal growth factors, fibroblast growth factors, transforming growth factors. And the like), prekallikrein, high molecular weight-kininogen, protein concentrates (e.g., clotting factor concentrates (e.g., alphanate FVIII concentrate, bioclate FVIII concentrate, monoclate-P FVIII concentrate, haemate P FVIII, von Willebrand Factor concentrate, helixate FVIII concentrate, hemophil-M FVIII concentrate, humate-P FVIII concentrate, hyante-C™, Porcine FVIII concentrate, koate HP FVIII concentrate; kogenate FVIII concentrate, FVIII concentrate, mononine FIX concentrate, fibrogammin p FXIII concentrate, and the like), and biologically active fragments thereof. It should be noted that the term "biologically active polypeptide agents" is meant to encompass active (e.g., processed) as well as activatable forms (e.g., zymogen) of polypeptides (e.g., where the polypeptides is an enzymes).

Exemplary ions that can find use as a biologically active agent include $Ca^{2+}$, $Mg^{2+}$, $Ag^+$, $Na^+$, $K^+$, $Zn^{2+}$, $PO_4^{3-}$, $SO_4^{2-}$, $NO_3^-$, and the like. Such ions can be provided in the form of a salt, e.g., a salt-loaded mesocellular foam.

Exemplary salts that can find use in the hemostatic compositions, and find particularly use in loading of mesocellular foams include, but are not limited to, aluminum sulfate, silver nitrate, calcium chloride, magnesium chloride, and the like.

Exemplary anti-inflammatory agents that can find use in the compositions disclosed herein include, but are not necessarily limited to, leukocyte migration preventing agents, silver sulfadiazine, acetylsalicylic acid, indomethacin, and Nafazatrom.

Other biologically active agents that can find use in the compositions disclosed herein include, but are not limited to antibiotics (e.g., bacteriocides, bacteristatics, fungicides, antivirals, and the like). Exemplary of such agents are $Ag^+$ ions, which may be provided as a silver salt, e.g. $AgNO_3$; β-lactams, cefoxitin, n-formamidoyl thienamycin, thienamycin derivatives, neomycin, metronidazole gramicidin, bacitracin, sulfonamides, aminoglycosides such as gentamycin, kanamycin, amikacin, sisomicin, or tobramycin, nalidixic acids and analogs such as norfloxican, combinations of fluoroalanine/pentizidone, nitrofurazones, and the like. Such antibiotics are generally selected so as to be compatible with the site of delivery (e.g., the depth of the wound to be treated, the site of the wound, and the like) and the microbial infection to be prevented and/or treated.

Further exemplary biologically active agents may include analgesics, anesthetics, steroids, vasoconstrictors, lymphokines, cytokines, vitamins, and the like.

Hemostatic Compositions and Devices

As noted above, mesocellular foams can be provided in combination with one or more additional biologically active agents, which hemostatically active agents being of particular interest.

Where the hemostatic composition is composed of a mesocellular foam with one or more additional biologically active agents, such may be provided in a variety of formats. For example, the biologically active agents (e.g., hemostatic agents) of the hemostatic compositions may be provided as a mixture (e.g., blended or admixed), may be provided as a coating of a substrate (e.g., where one or both of the biologically active agent and/or hemostatic composition is provided as a coating adhered to a substrate), or may be provided in a single package in the same or separate compartments of the package. The mesocellular foam and the additional biologically active agent(s) may also be provided in two or more packages that are to be opened and applied simultaneously to a wound.

In general, hemostatic compositions can be provided as a sterile composition, and as such are generally provided in a sealed, sterile container which maintains the sterility of the hemostatic composition until use. Where desired, the container can further provide for maintenance of a hydration state of the hemostatic composition, e.g., through use of materials that provide a water vapor-resistant barrier (e.g., mylar). For example, the hemostatic composition can be provided in a sterile container in the form of a sealable mylar foil bag.

The hemostatic compositions may further include fillers (e.g., aluminum sulfate) or thickening agents that facilitate the selective application of the hemostatic composition in various forms (e.g., as a paste, gel, powder, sprays, aerosols, cements, or erodable (e.g., biodegradable) solid member).

Dosage Forms and Carriers

The mesocellular foam hemostatic compositions of the disclosure can be provided in a variety of dosage forms, and, optionally, can be provided in combination with a variety of different, compatible carriers. Exemplary carriers include those which facilitate application to a wound, e.g., by facilitating delivery of the hemostatic composition from its packaging and to a wound, facilitating application and/or maintenance at a wound site, and the like. Accordingly, the hemostatic compositions, where compatible with the hemostatic activity of the hemostatic composition, can be provided as a dry formulation (e.g., a powder or other formulation that does not contain a liquid as a carrier), a paste, gel, or the like. In one embodiment, the hemostatic composition is provided as a dry, flowable dosage form that can be dispensed from a container (e.g., from a pouch or other sealed container). Hemostatic compositions can also be provided in aerosol form, and thus can be provided in a sterile spray (e.g., which can be provided in combination with a propellant, or in a sprayable solution). Hemostatic compositions can be stored in a suitable sterile container, e.g., in a water vapor-resistant container, optionally under an air-tight and/or vacuum seal.

Hemostatic Devices

The hemostatic compositions disclosed herein can be provided in connection with a device adapted for storage and/or delivery of a hemostatic composition to a bleeding wound. As discussed above, the hemostatic composition is generally provided in a sterile container, which may further provide a water vapor resistant barrier to prevent rehydration of material as may be desired.

The container can be in the form of a pouch (e.g., a mylar pouch), canister, tube, or other container. The container can include a frangible portion to facilitate rapid opening of the container to provide for quick access to and delivery of the hemostatic composition contained therein.

The hemostatic compositions can be provided in conjunction with a variety of different devices, which can be adapted to facilitate application of the hemostatic composition to a bleeding wound. For example, the hemostatic composition can be packaged in the same or separate container with one or more of a sterile sponge, gauze, bandage, swab, sprays, aerosols, gels, cements, compression bandage, pillow (e.g., to facilitate application to a head wound), sleeve (e.g., for covering a wound on a limb), and the like. In one embodiment, the device serves as a substrate for the hemostatic composition, where one or more of the hemostatic agents in the hemostatic composition can be adhered to the device. For example, the hemostatic composition can be provided on at least a surface of a blood-accessible surface of the device (e.g., as a surface coating), and/or within the device (e.g., permeating at least a portion of an absorbent material, such as gauze). It is to be understood that a "coating" is at least on the surface of the substrate to which it is applied, and may permeate beyond the surface, particularly where the substrate is an absorbent material.

Where the hemostatic compositions contain mesocellular foam and an additional biologically active agent, the mesocellular foam and other agent(s) may be present as a loose mixture (e.g., as in a pouch to be opened prior to use). In an embodiment of particular interest as described above, one or more biologically active agents are loaded on an mesocellular foam in the hemostatic composition. In another embodiment, the mesocellular foam-containing hemostatic composition is provided as a coating on a substrate, where the mesocellular foam may be optionally loaded with a biologically active agent (e.g., thrombin). Alternatively or in addition, a first hemostatic agent (e.g., mesocellular foam) may be provided as a coating on a substrate (e.g., bandage or sponge) and a second biologically active agent (e.g., hemostatic agent provided loose and in the same sealed packaging as the substrate).

Methods of Use of Hemostatic Compositions and Devices

The hemostatic compositions disclosed herein can be used to facilitate clotting of any external bleeding wound. As such, the hemostatic compositions can be used to enhance blood clotting in hemorrhaging blood of a subject in need, and at least temporarily stabilize a wound (e.g., at least temporarily stabilize a patient that might otherwise have died as a result of exsanguinations). Such methods generally involve contacting a hemostatic composition disclosed herein to a bleeding external or internal wound of a subject for a time sufficient to promote blood clot formation. The hemostatic composition can be contacted with a wound that is externally accessible by, for example, accessing the wound and pouring the hemostatic composition into the wound. Alternatively or in addition, the hemostatic composition can be delivered by applying a hemostatic device to the wound, where the device has an hemostatic composition coated on a substrate. Contact can be maintained through application of pressure, and may be held in place either by hand and/or through use of a bandage.

Contact is maintained at least until blood flow from the wound has slowed or has detectably ceased, i.e., until the wound is stabilized through formation of a clot. Once the clot is formed, the hemostatic composition can be removed from the wound. Where necessary, the wound can be irrigated to remove any loose hemostatic agent in the wound.

These methods are applicable to a variety of different types of wounds, which may have been inflicted intentionally or through accident and at any portion of the body amenable to application of a hemostatic composition disclosed herein. The hemostatic compositions find use in wounds of all degrees of severity ranging from bleeding skin surface wounds to wounds involving laceration of the femoral artery or other major artery or vein.

Subjects include any in need of treatment, and can include both human and veterinarian applications (e.g., mammals such as dogs, cats, livestock (e.g., cattle, horses, sheep, goats, etc.), and the like).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Celsius, and pressure is at or near atmospheric.

Example 1

Production of Mesocellular Foams

Mesocellular foam was prepared according to the method of Han et al. (supra). The porous architecture can be tailored with respect to surface area, pore size, pore size distribution, pore geometry, and inter-connectedness of pores.

Mesocellular foam was prepared by mixing the block copolymer P123 (BASF®), Tetra-ethyl ortho-silicate (TEOS), hydrochloric acid, 1,3,5 trimethyl benzene, and water in according with Han et al. (2007) Chem. Mater. 19:2292-2298. This solution was incubated in a hydrothermal bomb for 24 hours at 40° C. The hydrothermal bomb was then opened and ammonium fluoride was added. The solution was again incubated in a hydrothermal bomb for 24 hours at 180° C. The mesocellular foam was filtered and washed with deionized water and ethanol. The mesocellular foam was calcined at 550° C.

The average pore size of the resulting material was calculated based on N2 adsorption/desorption isotherms and calculated using the BET model. The results of the N2 adsorption/desorption isotherms and BET calculations are illustrated in FIG. 1. Mesocellular foam was prepared with two average pore dimensions of 177 Å (about 20 nm) and 315 Å (about 31 nm).

Figure 2:
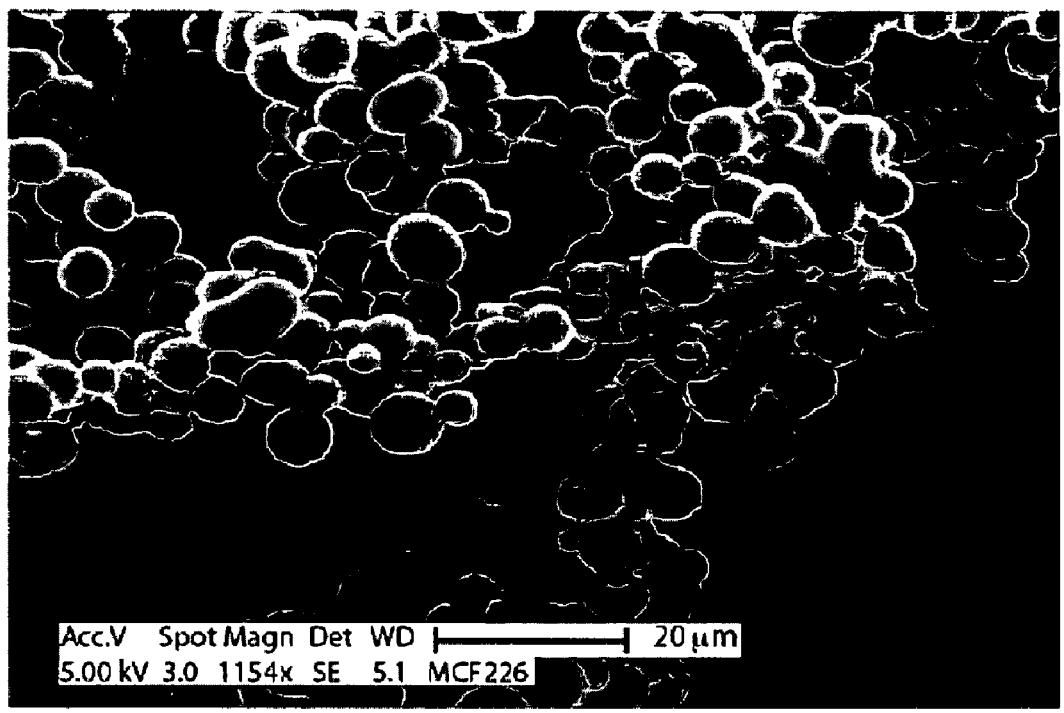
FIG. 2 illustrates results of scanning electron microscopy (SEM) of mesocellular foam.
Figure 3:
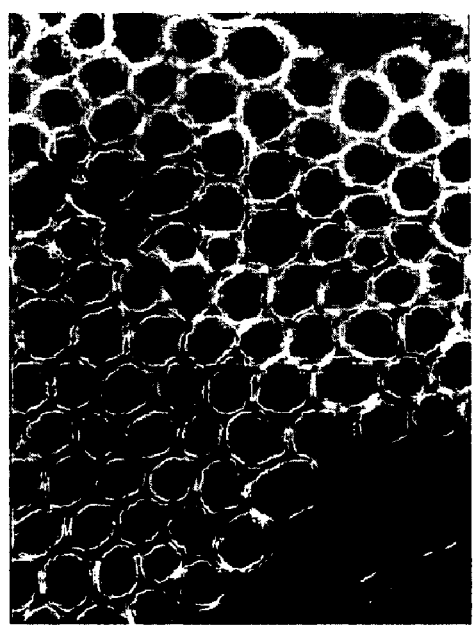
FIG. 3 illustrates results of transmission electron microscopy (TEM) of mesocellular foam.

As evidenced by Scanning Electron Microscopy (SEM), the mesocellular foam contained spherical particles. A representative scanning electron micrograph is illustrated in FIG. 2. The pores of mesocellular foam generated were arranged in a disordered geometry. A representative transmission electron micrograph is illustrated in FIG. 3.

Example 2

Effect of Mesocellular Foam on Clotting Time and Rate

A Haemoscope Thrombelastrograph™ was used to assess the clotting properties of all materials investigated. This instrument provides quantitative data regarding time until clot formation (R), rate of clot formation, (Alpha) and strength of the clot formed (MA) by measuring the torsion of a small sample of blood around a wire as the blood clots. First, 20 µl of 0.2 M $CaCl_2$ were added to a plastic cup heated to 37.5° C. Next, 340 µl of whole blood or plasma was added to the cup, followed immediately by addition of the test agent. Finally, the sample cup is loaded into position for commencement of the measurement. The time between sample loading and analysis is minimized to approximately 15 seconds.

Figure 4:
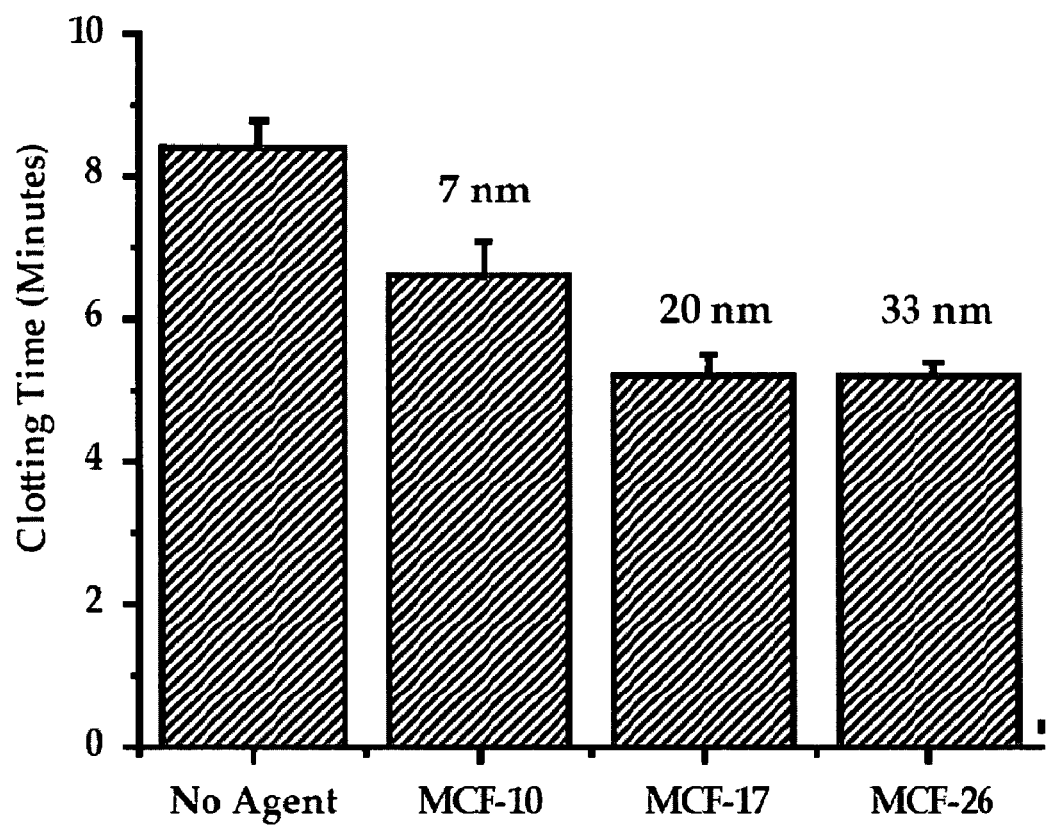
FIG. 4 is a graph showing clot formation time (R) of Mesocellular Foam of varying pore dimensions

As illustrated in FIG. 4, blood without any added hemostatic agent initiated clot formation (R time) of 8.5 minutes. The pore size of the mesocellular foams was calculated using the BET-BJH mathematical model based on the adsorption/desorption $N_2$ isotherms. This mathematical model assumes a spherical pore geometry. Thus even for non-spherically shaped pores, the BET-BJH model will determine one dimension to represent the size of the pore. MCF-10, which had an average pore size of 7 nm, initiated clot formation at 6.5 minutes. MCF-17, which had an average pore size of 20 nm, was observed to initiate clot formation at 5 minutes. MCF-26, which had an average pore size of 33 nm, initiated clot formation at 5 minutes.

Figure 5:
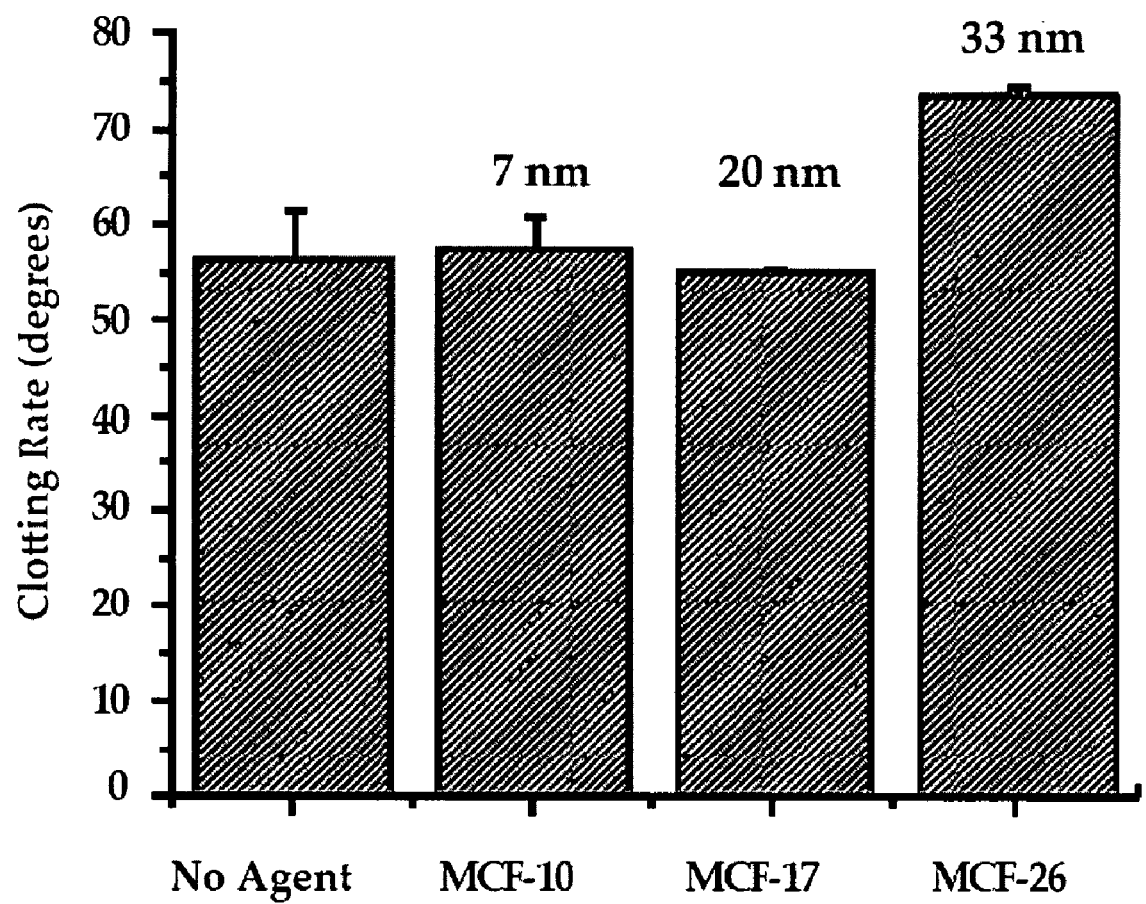
FIG. 5 is a graph showing rate of clot formation of Mesocellular Foam of varying pore dimensions.

As illustrated in FIG. 5, blood without any added hemostatic agent was observed to clot blood with a rate (a time) at 55°. MCF-10 (7 nm average pore size) clotted blood with a rate of 58°. MCF-17 (average pore size of 20 nm) clotted blood with a rate of 55°. MCF-26 (average pore size of 33 nm) clotted blood with a rate of 75°.

Example 3

Mesocellular Foam Having Bound Thrombin

The ability of mesocellular foam to bind the clotting enzyme thrombin, and the effects of thrombin-containing mesocellular foam on clotting activity of mesocellular foam, was tested. MCF-26 was added to a 2 mg/ml solution of bovine thrombin in 20 mM HEPES buffer at pH 5.2. MCF-26 (2 mg) was immersed in thrombin solution (1 ml-1.5 ml) overnight at 6-8 degrees C. The resulting product was washed with fresh buffer and centrifuged. The washing and centrifugation process was repeated until no detectable amount of thrombin was observed in the supernatant. The resulting thrombin-loaded MCF-26 contained 10-25% thrombin by weight as measured spectroscopically by the absorption of thrombin at 280 nm.

The activity of the thrombin-loaded mesocellular foams in promoting clotting was then tested. Clotting properties (clot time and clot strength) were assessed using a Haemoscope Thrombelastrograph™ and the assay described in Example 2 above. For hemostatic analysis, a slurry of thrombin-containing mesocellular foam product in the HEPES buffer was prepared. After the 2 mg of MCF with adsorbed thrombin (10-25% thrombin by weight) was washed and centrifuged as described in the above paragraph, the resulting product was dried. This dried, thrombin-containing MCF was resuspended in fresh HEPES buffer for a total volume of 50 µL. This resulting slurry was added to the 340 µL of blood and 20 µl of 0.2 M $CaCl_2$ used in the Thrombelastograph® analysis.

Figure 6:
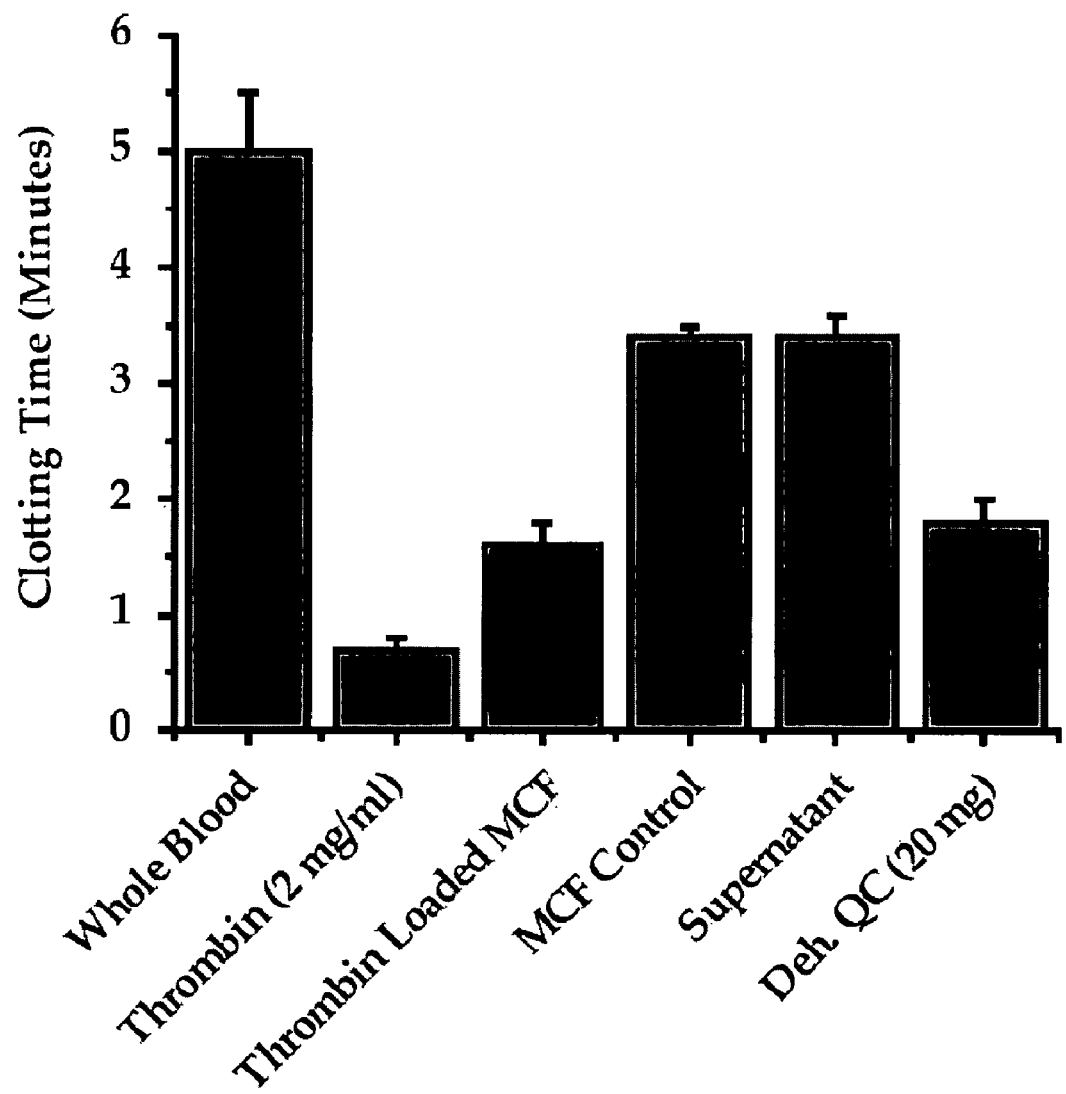
FIG. 6 is a graph showing clot formation time (R) of Mesocellular Foam with and without thrombin.

As illustrated in FIG. 6, MCF-26 without thrombin initiated clot formation in 3.5 minutes. In contrast, thrombin-loaded MCF-26 initiated clot formation in about 1.5 minutes. Thrombin alone initiated clot formation in 0.6 minutes. In comparison, whole blood without any hemostatic agent added was observed to initiate clot formation in 5 minutes. The supernatant extract of centrifuged whole blood was observed to initiate clot formation in 3.5 minutes. Dehydrated QuikClot® was observed to initiate clot formation in 1.7 minutes.

Figure 7:
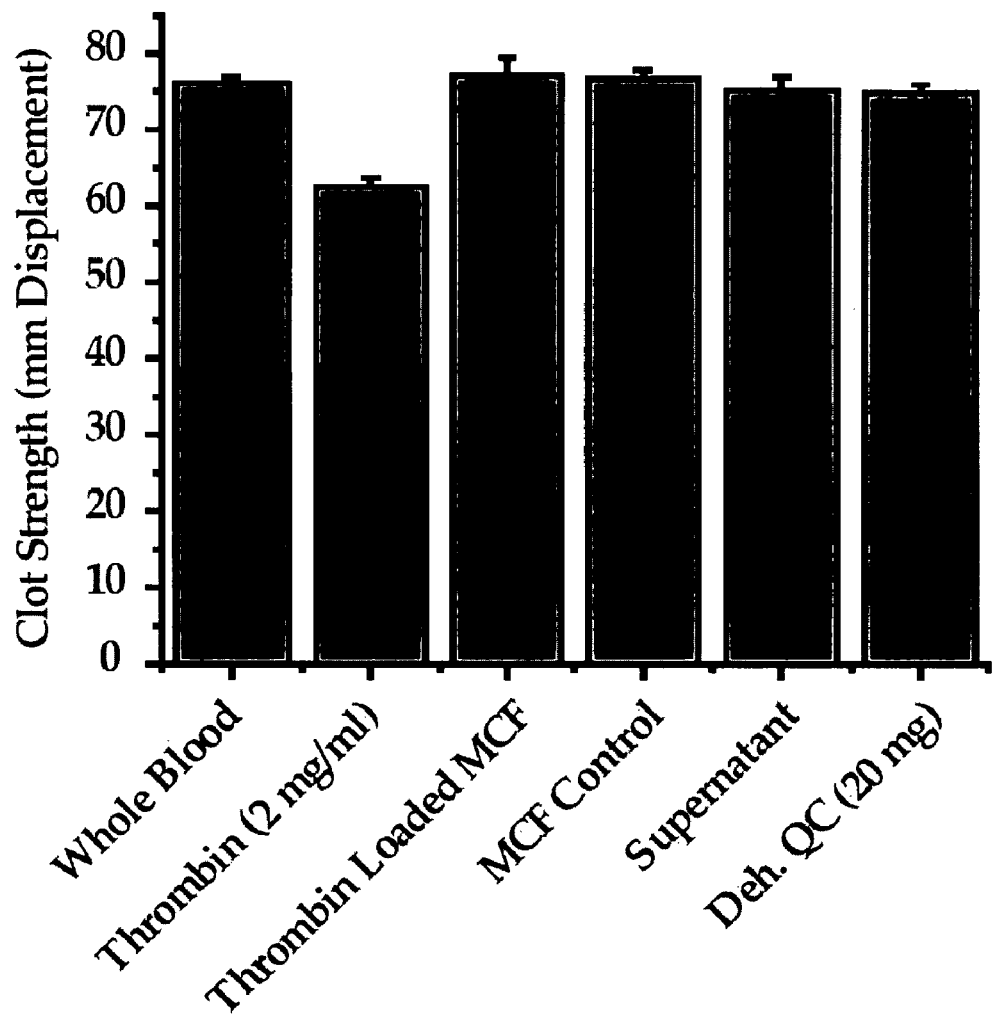
FIG. 7 is a graph showing rate of clot formation of Mesocellular Foam with and without thrombin.

Clots initiated by MCF-26 or thrombin-loaded MCF-26 exhibited similar clot strength. As illustrated in FIG. 7, MCF-26 without thrombin and thrombin-loaded MCF-26 each resulted in producing clots having a clot strength of about 75 mm. Thrombin alone was observed to produce clots having a clot strength of about 60 mm. In comparison, whole blood without any added hemostatic agent, supernatant extract of centrifuged whole blood, and dehydrated QUIKCLOT® (deh. QC) formed clots of a strength similar to that of MCF-26 and thrombin-loaded MCF-26.

The following materials and methods were used for Examples 4-8.

Example 4

Synthesis and Characterization of Mesocellular Foams with Varied Pore Sizes

To probe the effects of protein-accessible surface area on surface-activated blood clotting proteins, a series of mesocellular foams (MCFs) with varied pore window diameters were studied, while keeping other properties, such as surface chemistry, particle size, and morphology substantially the same. A series of silica-based MCFs with a range of pore sizes and pore opening diameters (i.e., pore window sizes) were synthesized according to published procedures (see Han, Y.; Lee, S. S.; Ying, J. Y., Spherical Siliceous Mesocellular Foam Particles for High-Speed Size Exclusion Chromatography. Chem. Mater. 2007, 19, 2292-2298), on one-quarter scale, using a calcination temperature of 550° C. for all materials.

Nitrogen sorption isotherms were obtained using a Micromeritics Tristar 3000 porosimeter. Prior to measurement, the samples were dried at 220° C. under nitrogen for 12 hours. The surface areas and pore volumes of the materials from each synthesis were calculated using the BET (Brunauer-Emmett-Teller) analysis, pore window sizes were determined using the Barret-Joyner-Halenda (BJH) method, and pore sizes were calculated also using the BJH method. Imaging to determine the particle size and morphology of the MCF materials was performed using an FEI XL30 electron microscope.

Nitrogen sorption data (Table 1) verified that the materials, designated by window size as MCF-6, MCF-11, MCF-21, MCF-26, and MCF-33, had a range of window and pore size distributions, pore volumes, and surface areas. While both the pore window opening and the pore diameter increased within this series of samples (MCF-6 to MCF-33), the pore window diameter may be the primary aspect that determines the ability of proteins to access the internal surface area of the material. The BET surface area decreased and the pore volume increased within the series of samples, indicating an increased amount of void space present in the samples with larger pore openings.

TABLE 1

Nitrogen sorption surface area characteristics for the MCF series

| Material | BJH window size (nm) | BJH pore size (nm) | BET Surface Area ($m^2$/g) | Pore Volume ($cm^3$/g) | Mass of Material Used in TEG (mg) |
| --- | --- | --- | --- | --- | --- |
| MCF-6  | 5.9  | 10.0 | 679 | 0.95 | 6.4 |
| MCF-11 | 11.2 | 24.5 | 739 | 1.53 | 4   |
| MCF-20 | 20.7 | 42.7 | 375 | 1.4  | 4.3 |
| MCF-26 | 26.4 | 41.9 | 364 | 2.3  | 2.6 |
| MCF-33 | 33.1 | 52.1 | 294 | 2.4  | 2.6 |

Figure 8:
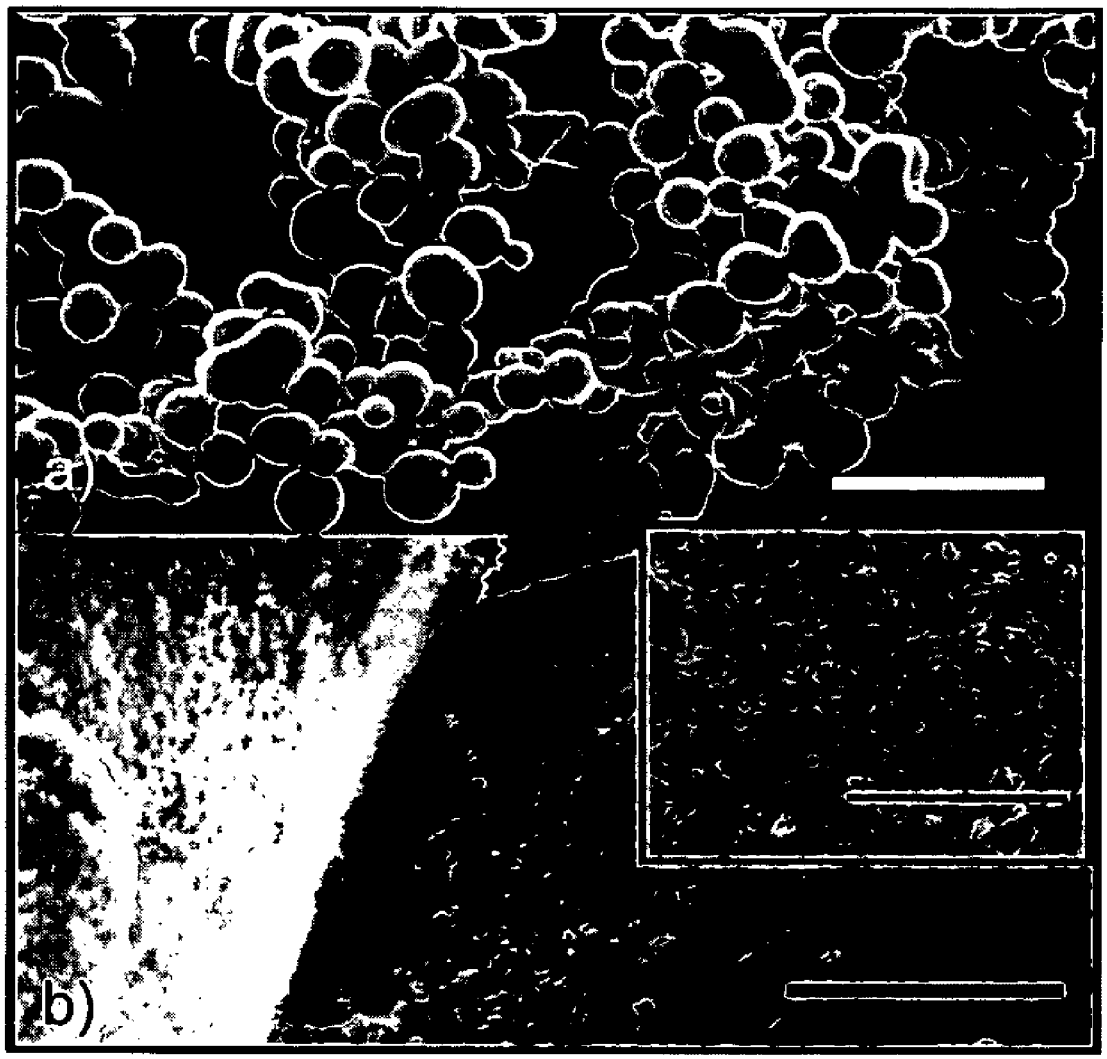
FIG. 8(a) is a SEM image showing the morphology of MCF-33. The scale bar represents 20 μm.
FIG. 8(b) is a higher resolution SEM image showing the surface morphology of MCF-33. The scale bar represents 1 μm, and the inset scale bar represents 250 nm.

Scanning electron microscopy (SEM) was used to confirm that particle size and morphology remained substantially the same within the MCF series, despite the varied window and pore size distributions among the samples. A representative SEM image of the MCF particle morphology, in this case MCF-33, is shown in FIG. 8a. The image indicates that the MCFs consist primarily of 5 µm-10 µm spheres with some fused spheres, and the higher resolution SEM images (FIG. 8b and inset) show the porous surface of MCF-33. These results show that the MCF materials synthesized are suitable for use as model materials to investigate the effects of pore window size on clot initiation.

Example 5

Determination of Clotting Activity of MCF Materials

Thrombelastograph (TEG) measurements in pooled human plasma (PHP) were used to determine the impact of MCF window size on the activation of blood coagulation proteins. The mass of material used in the analysis was adjusted for each MCF sample to account for variations in pore volume within the MCF series and to ensure that differences in clotting activity were due to changes in the pore opening diameter.

Frozen pooled human plasma (PHP) and Coumadin plasma (with an international normalized ratio of 2.4) were obtained from George King Biomedical and handled according to the package inserts.

A Haemoscope Thrombelastograph™ (TEG) was used to compare the clotting properties of the variable-pore MCF and QuikClot hemostatic agents. The TEG measures several parameters that may be relevant to the effectiveness of a hemostatic material, including time until initial clot formation, and the rate of clot formation, by measuring the torsion of a small sample of blood around a wire during coagulation. The TEG was operated as follows: First, 20 µl of 0.2 M $CaCl_2$ was added to the TEG cup which was heated to 37.0° C. Then, 340 µl of plasma was added to the cup, followed immediately by addition of the clotting agent from a 1 dram glass vial. The sample cup was then loaded into position for commencement of the measurement. In order to determine the effects of pore size alone on the clotting parameters of human plasma, the total external volume of MCF spheres added to the plasma was kept substantially the same by keeping the total pore volume at about 0.006 $cm^3$ for each sample. Therefore, a different mass of each MCF was added to the plasma, according to their respective pore volume. Thus, the masses added were: 6.4 mg of MCF-6, 4 mg of MCF-11, 4.3 mg of MCF-20, 2.6 mg of MCF-26, and 2.6 mg MCF-33.

QuikClot was handled and stored in an argon dry box. Sealed QuikClot packages (Z-Medica Corporation, Wallingford, Conn.) were transferred into the argon dry box before opening and 20 mg of QuikClot was measured into 1 dram glass vials. The vials were sealed and removed from the dry box within 30 minutes of use.

Figure 9:
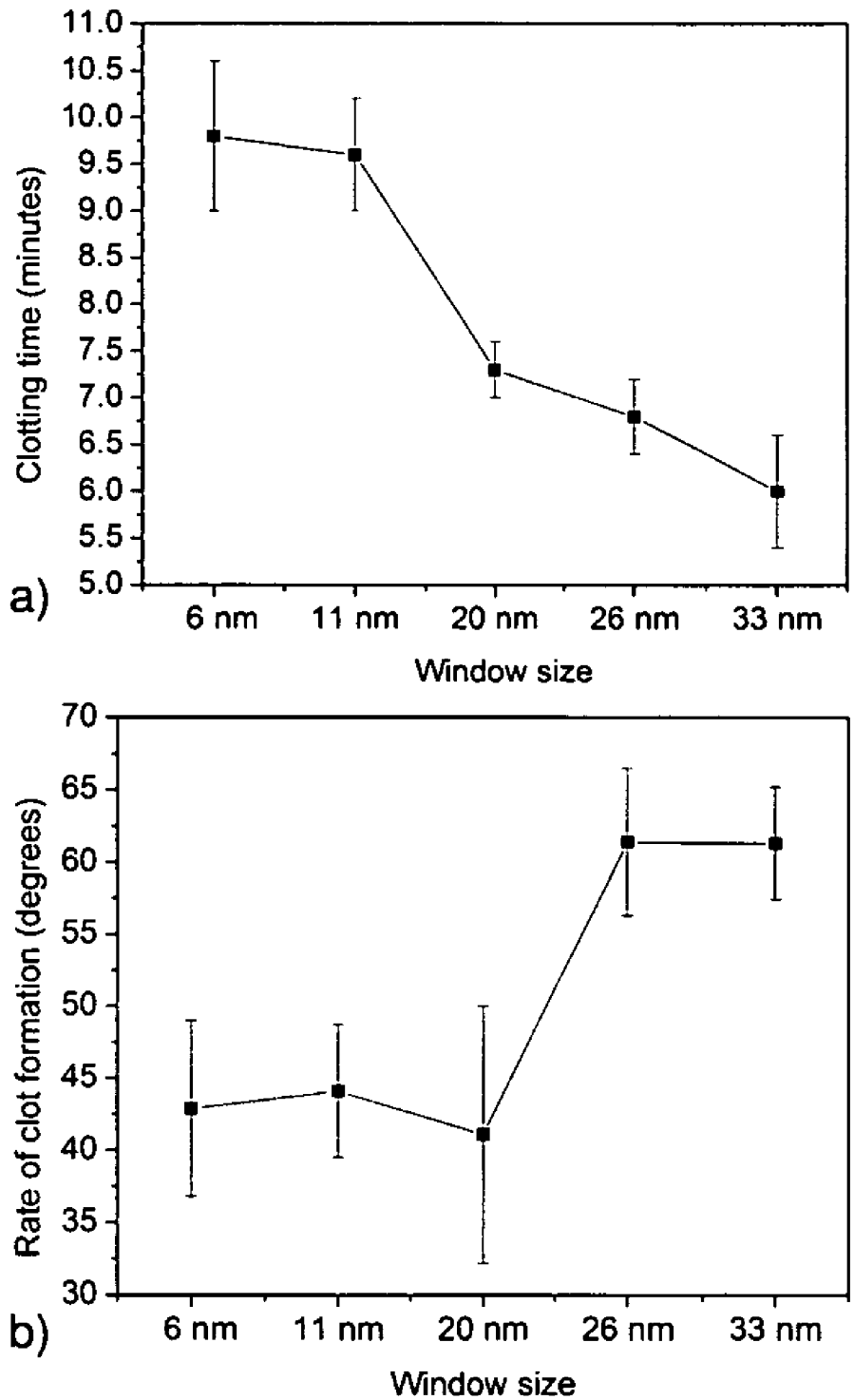
FIG. 9(a) is a graph of time to clot formation (minutes) over MCF pore window size (nm).
FIG. 9(b) is a graph of the rate of clot formation (degrees) over MCF pore window size (nm).

FIG. 9a shows the time to clot initiation of pooled human plasma after exposure to the MCF samples of each window size. As the window size increased from 6 nm to 33 nm, the average time to blood clot initiation decreased from 9.8 minutes to 6 minutes. In addition, the results indicate a sharp decrease in clot initiation times with pore sizes greater than 11 nm. Furthermore, the rate of clot formation (FIG. 9b), which is related to the time required for the blood clot to reach maximum clot strength, increased significantly when the average window size of the material was greater than 20 nm.

The dramatic effect of MCF pore window size on blood clot initiation time and the rate of blood clot formation in human plasma may be facilitated by the increased protein-accessible surface area available with larger pore opening diameters. Within the series of MCF samples studied here, the lower-surface-area materials (as determined by nitrogen sorption isotherms, Table 1) resulted in faster clot formation, which is contrary to the paradigm that clotting time decreases with increasing pro-coagulant material surface area.(see e.g., Vogler, E. A.; Graper, J. C.; Harper, G. R.; Sugg, H. W.; Lander, L. M.; Brittain, W. J., Contact Activation of the Plasma Coagulation Cascade. *J. Biomed. Mater. Res.* 1995, 29, (8), 1005-1016; and Chatterjee, K.; Vogler, E. A.; Siedlecki, C. A., Procoagulant activity of surface-immobilized Hageman factor. *Biomaterials* 2006, 27, 5643-5650). The results indicate that the pore window size, rather than the surface area, as measured by BET surface area, is a more relevant parameter to consider in the design of porous wound-dressing materials for hemorrhage control. In particular, a pore window size of at least about 20 nm may facilitate fast blood-clot activation.

Example 6

Thrombin Loading

The mass of bovine thrombin (Aldrich, 236 NIH units/mg) adsorbed to each MCF sample was determined by measuring the absorbance of a 2 mg/ml thrombin solution in quartz cuvettes prior to and after exposure to the solid. 0.6-1 ml of 2 mg/ml thrombin in HEPES buffer (20 mM, pH 5.3) was added to 2-4 mg MCF in a plastic 1.5 ml centrifuge tube. Thrombin adsorption to the sides of the plastic centrifuge tubes in which the thrombin-immobilization studies were carried out was found to be negligible. The quantities used in FIG. 10a were 0.8 ml of 2 mg/ml thrombin solution and 4 mg MCF-33. The MCF loading capacity for thrombin was calculated as follows: the absorbance value of 0.75 corresponded to 1.6 mg thrombin in this experiment. After incubating with 4 mg MCF, the absorbance of the solution decreased by 0.25 units, indicating that 0.53 mg thrombin adsorbed to 4 mg of MCF material, corresponding to a loading of 13% w/w. The resulting MCF-thrombin (MCF-T) material was then washed four times with HEPES buffer using centrifugation and the supernatant was removed. In all cases, after two centrifugation steps, thrombin was not detectable in the supernatant by UV/vis.

Figure 10:
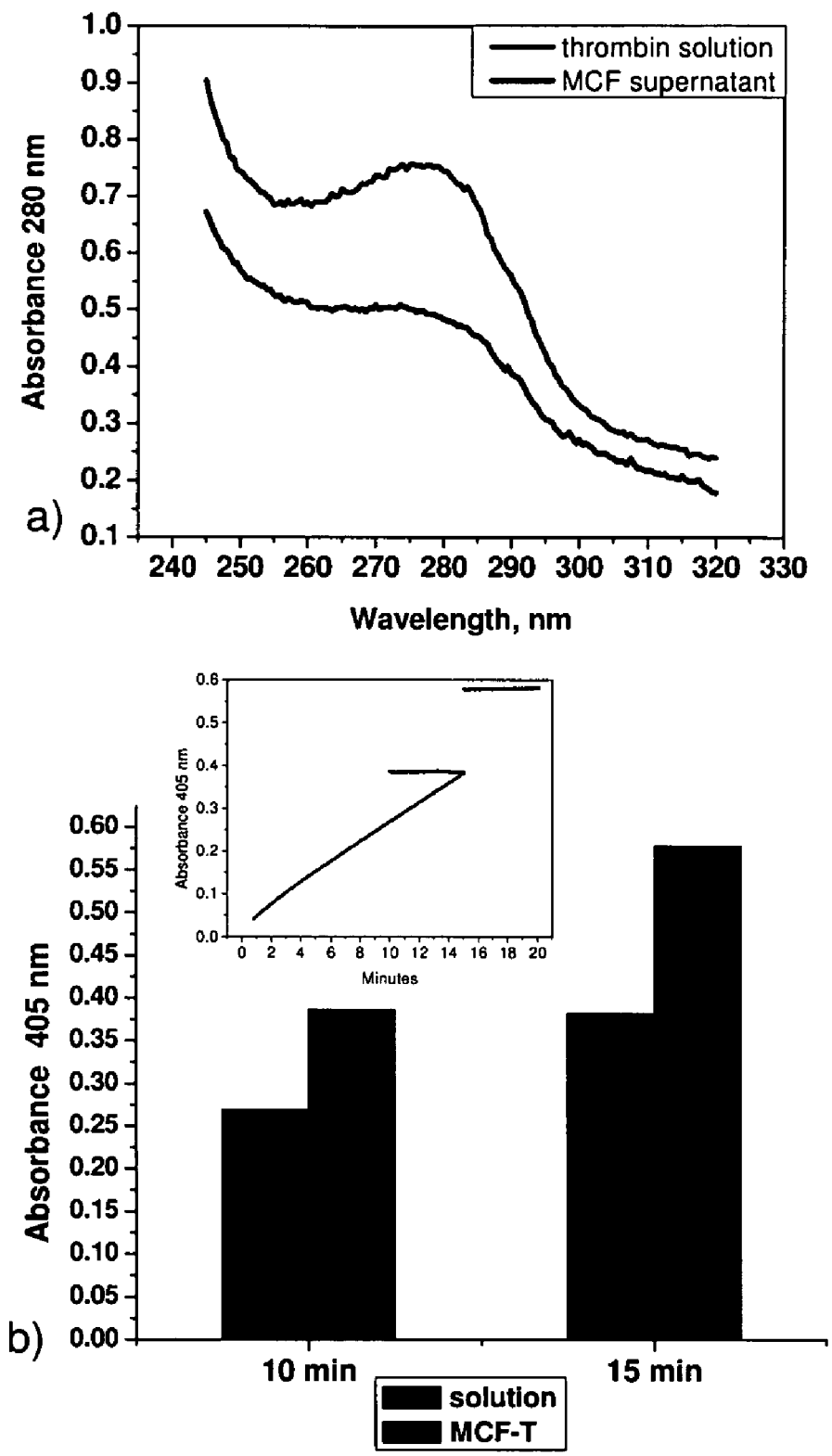
FIG. 10(a) is a graph of the optical absorbance measurement indicating degree of thrombin immobilization on MCF-33.
FIG. 10(b) is a graph showing the comparison of enzymatic activity of 0.4 mg thrombin in solution versus thrombin adsorbed to MCF as indicated by absorbance at 405 nm.

The loading efficiency of bovine thrombin (pI 7.1) on equal masses (1 mg) of MCF-33 and Gelfoam, commercial gelatin sponge, was determined at pH values between 9.4 and 5.4 by comparing the optical absorption at 280 nm of a thrombin solution before and after exposure to each material. We found that the optimal pH for immobilizing thrombin on MCF was in the range between pH 5.4 and 6.4, which enabled an enzyme loading capacity of 13% w/w (FIG. 10a). However, the maximum loading capacity determined for the Gelfoam sponge was only 2% w/w at pH 6.4 (data not shown).

These results indicate that the porous network of MCF-33 yields a much higher thrombin loading capacity than the same mass of the gelatin sponge. The large pore opening diameter of MCF-33 facilitates the transport of thrombin into the interior of the material and the large pore volume allows for retention of thrombin within the porous network of the material.

Example 7

Determination of the Enzymatic Activity of MCF-Thrombin

In order to determine whether the thrombin was irreversibly bound to the MCF and retained its activity, a chromogenic substrate for thrombin, β ala-gly-arg-p nitroanalide diacetate (Sigma-Aldrich), which is a colorimetric substrate specific to thrombin, was used (see Prasa, D.; Svendsen, L.; Sturzebecher, J., Inhibition of Thrombin Generation in Plasma by Inhibitors of Factor Xa. *Thromb Haemost* 1997, 78, 1215-1220). The activity of thrombin in the presence of the colorimetric substrate in this assay corresponds to the rate of change in optical absorbance of the substrate solution at 405 nm. To prevent the MCF material from interfering with absorbance measurement, each sample was centrifuged and the supernatant was analyzed. 100 μl of substrate solution [3 mg/ml in HEPES 7.4 buffer (20 mM, 0.15 M NaCl), pH 7.4] and 800 μl HEPES pH 7.4 was added to 4 mg MCF-T pellet (prepared as described above) and inverted several times. After 8 minutes, the MCF-T suspension was visibly yellow, and was centrifuged for 2 minutes and the supernatant removed in order to determine the amount of substrate cleaved by thrombin after 10 minutes. To determine the 15 minute time point, the MCF-T suspension was immersed in the substrate solution for 13 minutes prior to two minute centrifugation. In order to compare the activity of the immobilized thrombin to that in solution, a volume of 2 mg/ml thrombin solution necessary to equal the mass of thrombin adsorbed to the MCF material was used under the same assay conditions. This volume (e.g. 265 μl for 13% thrombin loading on 4 mg of MCF) was added to 100 μl chromogenic substrate and 800 μl HEPES pH 7.4, and the absorbance was measured at 405 nm for 15 minutes. To control for the effects of dilution which occurred by adding this additional 265 μl solution to the substrate solution, the activity of the solution phase thrombin was compared to MCF-T which was diluted by an additional 265 μl HEPES 7.4 buffer.

In all cases, the activity of the MCF-T was greater (about 20-30% higher absorbance values due to MCF-T than solution phase thrombin after 15 minutes) than the same mass of thrombin in solution. To test for long-term leaching of thrombin from MCF, the activity of the MCF-T supernatant was measured after 12 days, and negligible activity was found, while the MCF-T material retained ⅓ of the initial activity after 12 days. To determine whether the high ionic strength of blood might cause thrombin to be released from the MCF pores, MCF-T was immersed in simulated body fluid (composition i; see Oyane, A.; Kim, H.-M.; Furuya, T.; Kokubo, T.; Miyazaki, T.; Nakamura, T., Preparation and assessment of revised simulated body fluids. *Journal of Biomedical Materials Research* 2003, 65A, (2), 188-195) for 30 minutes. The sample was centrifuged to remove the MCF-T and the activity of thrombin in the supernatant was measured and negligible activity was found.

Representative results from these experiments are shown in FIG. 10b. As shown in FIG. 10b, the MCF-T supernatant solutions (resulting from exposure to approximately 400 μg thrombin adsorbed to 4 mg MCF) had higher absorbance values at 405 nm (i.e., about 20-30% greater) after ten and fifteen minute time intervals than 400 μg solution-phase thrombin (in 200 μl buffer). This indicates that immobilized thrombin catalyzed the cleavage of the chromogenic substrate at a higher rate than solution-phase thrombin. FIG. 10b (inset) shows the time dependence of the data from which FIG. 10b was derived. The trace with a positive slope in FIG. 10b (inset) shows the absorbance change due to cleavage of the substrate by solution-phase thrombin during the initial 15 minutes. The horizontal traces in FIG. 10b (inset) represent the time-dependent absorbance of chromogenic substrate in the MCF-T supernatant which was removed from the MCF-T by centrifugation after 10 and 15 minutes. As can be seen in FIG. 10b (inset), the absorbance of the MCF-T supernatant at 405 nm did not change significantly with time after the removal of the MCF-T, indicating that the thrombin activity was localized to the MCF-T. The lack of absorbance change in the MCF-T supernatant at both 10 and 15 minute time points indicates that the thrombin was confined to the surface of the MCF-T. These data are consistent with highly active, irreversibly adsorbed thrombin present in the pores of the MCF materials.

Example 8

Characterization of Thrombin-Loaded MCFs in Human Plasma

The clotting performance of 20 mg dehydrated QuikClot, 2 mg MCF-33 (a control), and 2 mg of MCF-33 immobilized with thrombin in both pooled human plasma and in Coumadin plasma using TEG were compared. The MCF-T was prepared as described above. To ensure that the MCF control had substantially the same surface chemistry to MCF-T, the MCF control was also immersed in HEPES pH 5.3 buffer overnight and washed extensively using centrifugation with HEPES pH 7.4 buffer. After removing the supernatant, the MCF samples (2 mg) were resuspended in 50 μl of HEPES pH 7.4 buffer and were added to the plasma as a slurry using a 200 μl pipette. Control experiments verified that the addition of 50 μl of the HEPES pH 7.4 buffer alone did not significantly change the plasma clotting times.

Figure 11:
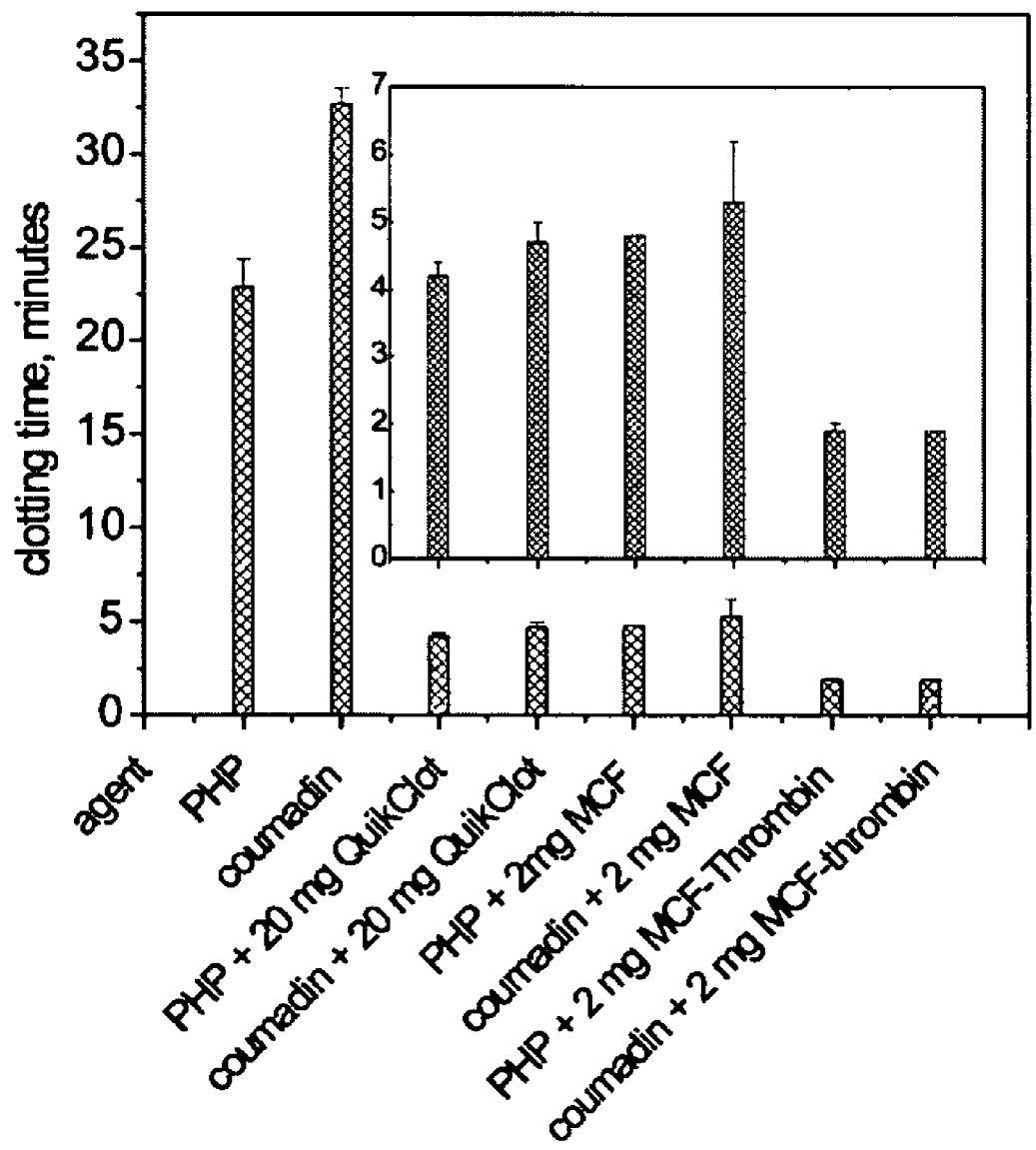
FIG. 11 is a graph of clotting times of pooled human plasma (PHP) and Coumadin plasma alone (left) after exposure to MCF, MCF-thrombin, and QuikClot clotting agents.

The results of the above in vitro evaluation of MCF-T are shown in FIG. 11. The left side of FIG. 11 shows that PHP clots significantly faster than the Coumadin plasma, which is expected due to the lower concentrations of vitamin K dependent clotting factors in the Coumadin plasma. FIG. 11 (inset) shows that adding 20 mg of dehydrated QuikClot reduced the clotting times of both PHP and Coumadin plasma. Only 2 mg of MCF-33 (suspended in 50 μl buffer) accelerated blood clot formation similarly to 20 mg of QuikClot. The fact that an order of magnitude lower mass of MCF-33 was required to demonstrate in vitro effectiveness similar to QuikClot may be due to the comparatively higher degree of protein-accessible surface area of MCF-33. The majority of the surface area in QuikClot is in the micropore size range, and is not accessible to proteins. As a result, a smaller mass of the MCF-33 material was needed to achieve the same clotting effect of the nano-porous QuikClot material.

The immobilization of thrombin in the pores of MCF decreased the plasma clotting time by more than half compared with the same mass of MCF, and resulted in an extremely active clotting material. Furthermore, the effectiveness of MCF-T was identical both in the PHP and in Coumadin plasma.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A hemostatic composition comprising a hemostatically effective amount of a sterile, mesocellular oxide foam,
   wherein the mesocellular foam is characterized by an average pore size of from about 10 nm to 100 nm, and wherein the mesocellular foam has an average pore window size of at least 11 nm, and
   wherein the mesocellular foam comprises a bound biologically active agent comprising a clot promoting agent.

2. The hemostatic composition of claim 1, wherein the mesocellular foam has an average pore window size of at least 20 nm.

3. The hemostatic composition of claim 1, wherein the mesocellular foam has an average pore window size ranging from about 11 nm to about 35 nm.

4. The hemostatic composition of claim 1, wherein the mesocellular foam has an average pore volume of at least 1 cm$^3$/g.

5. The hemostatic composition of claim 1, wherein the mesocellular foam has an average pore volume of at least 1.4 cm$^3$/g.

6. The hemostatic composition of claim 1, wherein the mesocellular foam has an average pore volume ranging from about1 cm$^3$/g to about 2.5 cm$^3$/g.

7. The hemostatic composition of claim 1, wherein the biologically active agent is covalently bound in or on the mesocellular foam.

8. The hemostatic composition of claim 1, wherein the biologically active agent is non-covalently bound in or on the mesocellular foam.

9. The hemostatic composition of claim 1, wherein the clot promoting agent is thrombin.

10. A thrombin-loaded mesocellular oxide foam comprising at least 5% by weight thrombin, wherein the mesocellular foam is characterized by an average pore size of from about 10 nm to 100 nm, and wherein the mesocellular foam has an average pore window size of at least 11 nm.

11. The thrombin-loaded mesocellular foam of claim 10, wherein the mesocellular foam comprises at least 10% to 25% by weight thrombin.

12. A medical device comprising:
    the hemostatic composition of claim 1 or 10; and
    a sterile substrate on which the hemostatic composition is disposed.

13. The device of claim 12, wherein the substrate is adapted for delivery of the hemostatic composition to a bleeding wound.

14. The device of claim 13, wherein the substrate is a bandage, gauze, or sponge.

15. A method of clotting blood flowing from a wound, comprising:
    applying to a wound in a subject the hemostatic composition of claim 1 or 12 to a bleeding wound of the subject; and maintaining the hemostatic composition in contact with the wound for a period of time sufficient to at least initiate blood clotting.

16. A method of making a hemostatic composition, the method comprising:

contacting a mesocellular oxide foam characterized by an average pore size of from about 10 nm to 100 nm and an average pore window size of at least 11 nm with a solution containing a biologically active agent, said contacting being for a time sufficient to provide for adsorption or absorption of the biologically active agent to the mesocellular foam;

wherein a hemostatic composition comprising the mesocellular oxide foam and bound biologically active agent is produced, and wherein the biologically active agent comprises a clot promoting agent.

* * * * *